(12) United States Patent
Stoffel (10) Patent No.: US 7,240,573 B2
(45) Date of Patent: Jul. 10, 2007

(54) SAMPLING DEVICE AND SAMPLING METHOD

(75) Inventor: Jean-Pierre Stoffel, Blodelsheim (FR)

(73) Assignee: Aeromatic-Fielder AG, Bubendorf (CH)

( * ) Notice: Subject to any disclaimer, the term of this patent is extended or adjusted under 35 U.S.C. 154(b) by 273 days.

(21) Appl. No.: 10/344,649

(22) PCT Filed: Feb. 11, 2003

(86) PCT No.: PCT/IB03/00447

§ 371 (c)(1),
(2), (4) Date: Aug. 26, 2004

(87) PCT Pub. No.: WO2004/072543

PCT Pub. Date: Aug. 26, 2004

(65) Prior Publication Data

US 2005/0188774 A1    Sep. 1, 2005

(51) Int. Cl.
*G01N 1/00*    (2006.01)

(52) U.S. Cl. .................... 73/863.86; 73/863; 73/864.63

(58) Field of Classification Search ............ 73/864.63, 73/863.86, 863; 251/149.6; 604/905
See application file for complete search history.

(56) References Cited

U.S. PATENT DOCUMENTS

| | | | | |
|---|---|---|---|---|
| 1,335,880 | A | * | 4/1920 | Dodds .................. 175/246 |
| 1,830,012 | A | * | 11/1931 | Barrett et al. ............... 175/246 |
| 3,528,294 | A | * | 9/1970 | Manevy .................... 73/863.42 |
| 4,150,575 | A | * | 4/1979 | Magorien ................ 73/863.86 |
| 4,484,482 | A | | 11/1984 | Fournier et al. |
| 4,580,452 | A | * | 4/1986 | Masson .................... 73/863.86 |
| 4,689,306 | A | * | 8/1987 | Redikultsev et al. .... 435/309.2 |
| 4,699,356 | A | * | 10/1987 | Hargrove et al. ........ 251/149.6 |
| 2004/0011983 | A1 | * | 1/2004 | Maiville et al. ......... 251/149.6 |

FOREIGN PATENT DOCUMENTS

| | | |
|---|---|---|
| DE | 40 34 700 A1 | 5/1992 |
| DE | 43 01 174 A1 | 7/1994 |
| DE | 197 35 586 C1 | 12/1998 |
| EP | 0 141 940 A1 | 5/1985 |
| FR | 2 656 694 | 7/1991 |
| JP | 9-79949 | 3/1997 |

* cited by examiner

*Primary Examiner*—Hezron Williams
*Assistant Examiner*—Samir M. Shah
(74) *Attorney, Agent, or Firm*—Sughrue Mion, PLLC (57) ABSTRACT

A sampling device (1) comprises a sampling container (4) for reception of a sample volume and a connecting piece (7) adapted to be connected to a fitting (2) mounted on a processing installation. The connecting piece (7) has a sample passage which is provided with a stationary valve part (12) and a corresponding valve member (14) which is displaceable between a closed and an open position. The stationary valve part (12) and the displaceable valve member (14) are integrated in the sampling container (4). The valve member (14) is spring-loaded towards its closed position and adapted to be automatically displaced to its open position upon connection of the connecting piece (7) with the fitting (2).

26 Claims, 4 Drawing Sheets

SAMPLING DEVICE AND SAMPLING METHOD

CROSS-REFERENCE TO RELATED APPLICATIONS

The present application claims the benefit of priority from the International Patent Application No. PCT/IB03/00447 filed on 11 Feb. 2003.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

The present invention relates to a sampling device comprising a sampling container for reception of a sample volume and a connecting piece adapted to be connected to a fitting mounted on a vessel or pipe of a processing installation or the like, the connecting piece having a sample passage which is provided with a stationary valve part and a corresponding valve member which is displaceable between a closed position, in which it abuts the stationary valve part and closes the sample passage, and an open position, in which the sample passage is open.

EP 0141 940 corresponding to U.S. Pat. No. 4,580,452 discloses a sampling container being connected through a pipe to a manually operated sampling valve which may be screwed into a fitting mounted on a conduit forming part of a chemical plant installation. The fitting is also provided with a manually operated valve in order to close the outlet from the conduit when the sampling valve is not connected to the fitting. To take a sample, firstly the sampling valve must be screwed into the fitting, the two valves must be opened and subsequently closed, and the sampling valve must be disconnected from the fitting. Obviously, this procedure is time-consuming, and furthermore there is a risk of forgetting to close one of the valves after having taken a sample, whereby possibly hazardous product could escape from the sampling system. Additionally, the configuration of the sampling container and its connected valve is awkward to handle and susceptible to damages if dropped, which may result in product spillage. Furthermore, the device is suitable for the sampling of fluids only, as products such as powder or granules would clog up the passages through the valves and the pipe.

DE 40 34 700 describes a dual-valve system for the taking of a fluid sample from a pipe system. A first valve member in the form of a truncated cone is arranged in a pipe rotatably about an axis perpendicular to the direction of flow in the pipe and has a through passage in-line with the pipe opening when set to its open position. In this open position, a sample may be taken from the pipe through a second valve arranged in a connection piece inserted in the lower side of the truncated cone. After having taken a sample, both valves are closed, and the internal product-contaminated surfaces which are situated between the two closed valves are cleaned by means of a spray device. However, this procedure is most cumbersome and time-consuming. Furthermore, the system also has the disadvantage that the second valve must be closed manually in order to prevent spillage of the product sampled. The sampling container protrudes radially from the second valve and makes the device awkward in use.

DS 43 01 174 discloses a sampling valve having a semi-cylindrical valve member arranged rotatably in a bore extending tangentially to the inner surface of a pipe wall. An external sampling container is screwed into a fitting which is mounted on the outside of the pipe wall and is in fluid connection with the bore through a passage. When the valve member is in its open position, a fluid may pass from the pipe to the sampling container. After removing the sampling container from the fitting, the container is open to the surroundings and consequently product may be spilled.

DE 197 35 586 shows a sampling valve having an outlet opening through the wall of a pipe and a corresponding valve member which by means of a spindle is manually operable from the outside of the pipe. A sampling container for the reception of a fluid may be held under the outlet opening when the valve is opened.

BRIEF SUMMARY OF THE INVENTION

The object of the present invention is to provide a sampling device whereby the risk of product spillage is reduced.

In view of this, the sampling device according to the invention is characterized in that the stationary valve part and the valve member are integrated in the sampling container, and in that the valve member is spring-loaded towards its closed position and adapted to be automatically displaced to its open position upon connection of the connecting piece with the fitting.

In this way, the sampling contain will always be automatically closed by means of the valve member upon disconnection of the container from the fitting, and product spillage through the connection piece may be hindered, even if the container should be dropped. Furthermore, the integrated design of the stationary valve part and the valve member in the sampling container provides for a more robust construction and a device which is easier and therefore safer to handle. Consequently, also the risk of dropping the device is reduced.

Because the integrated design ensures a short and unimpeded path for the product to be sampled, the sampling device according to the present invention is very suitable for the sampling of powders, granules and the like, as well as any type of fluid or flowable product.

In an advantageous embodiment, the displaceable valve member has a conical sealing surface corresponding to a conical sealing surface on the stationary valve part. This ensures a good sealing effect.

In a simple and therefore reliable embodiment, the connecting piece is adapted to be displaced in a longitudinal direction of the container during at least part of the operation of connecting it to the fitting, and the displaceable valve member is adapted to abut an edge of the fitting during at least part of said displacement. The valve member will then be displaced in the sampling container to its open position as a result of the displacement of the connecting piece in the direction against the fitting.

In a preferred embodiment, the connecting piece is adapted to be screwed onto the fitting. This ensures a strong connection between the connecting piece and the fitting. The device may in this way be designed explosion proof, for instance in order to be able to withstand an internal pressure of 10 bars.

In an advantageous embodiment, the sampling container comprises an outer container and an inner container, the inner container is arranged displaceably in a longitudinal direction of the outer container, the outer container is at a first end formed integrally with the connecting piece and is at a second end provided with a bottom, the inner container is at a first end formed integrally with an annular sealing surface, thereby forming the displaceable valve member, and has at a second end a bottom in which a spindle passage is provided, a spindle has a first end which is provided with the stationary valve part and a second end which is fixed to the bottom of the outer container, and the spindle passage is arranged tightly around and displaceably along the spindle. By the provision of two containers arranged one inside the other, an even more robust construction is achieved, especially in terms of the ability to withstand a high internal pressure, but also considering the risk of dropping the container. Furthermore, the device is simple to manufacture because very few components are required.

In an embodiment, the outer length of the outer container is between 100 mm and 300 mm, the outer diameter of the outer container is between ½ and ⅔ of the outer length of the outer container, and the smallest diameter of the annular sealing surface of the inner container is between ¼ and ⅔ of the outer diameter of the outer container.

In an advantageous embodiment, the outer container and the inner container are formed from Plexiglass®, glass, tempered glass or the like, and the stationary valve part is formed from polytetrafluoroethylene or the like. This configuration allows visual inspection of the product sample through the Plexiglass or glass, and a good sealing effect is obtained between Plexiglass or glass and polytetrafluoroethylene.

In a further embodiment, the sampling device comprises a fitting mating the connecting piece and having an installation end adapted to be installed onto the vessel or pipe of said processing installation or the like, and the fitting has a tubular part provided with an inner shielding member adapted to shield the stationary valve part in the connected state of the connecting piece and the fitting. Thereby the outward surface of the stationary valve part is shielded against the sample product during taking of the sample and consequently this surface will be free from product after removal of the sampling container from the fitting. This may be an advantage especially in case of hazardous products. Further, the product flow may be guided and thereby facilitated by the shielding member.

In a further embodiment, the tubular part of the fitting is provided with a covering member adapted to cover the displaceable valve member in the connected state of the connecting piece and the fitting. Thereby also the displaceable valve member will be free from product after removal of the sampling container from the fitting and the cleanliness of the device is further improved.

In a further embodiment, the shielding member is adapted to seal against the covering member in the disconnected state of the connecting piece and the fitting. This prevents product from leaking from the fitting after removal of the sampling container from the fitting. Especially in case of toxic products, this may be an advantage.

In a further embodiment, a circumferential contour of the shielding member fits a circumferential contour of the stationary valve part, the shielding member is adapted to be displaced with the stationary valve part against a spring-load during at least part of the operation of connecting the connecting piece to the fitting, a circumferential contour of the covering member fits a circumferential contour of the displaceable valve member, the covering member is fixedly mounted in the fitting, the circumferential contour of the shielding member fits the circumferential contour of the covering member, and the circumferential contour of the stationary valve part fits the circumferential contour of the displaceable valve member. Thereby a product sample may be taken out from a processing installation in a fully contained way, so that, after disconnection of the sampling container from the fitting, substantially no product will leak to the surroundings of the fitting and the sampling container. In this way, the operator will practically not be exposed to the product sampled.

The shielding member may have a conical sealing surface corresponding to a conical sealing surface on the covering member. This ensures improved sealing effect.

In a further embodiment, the shielding member is spring-loaded against the covering member by means of a spring located in a tube element in which a spindle of the shielding member is guided, the tube element is guided axially in the tubular part of the fitting, and the tube element is fixed in a plate adapted to abut an edge of a flange on the vessel or pipe of the processing installation or the like, in the mounted state of the fitting on said flange. Thereby the shielding member will be automatically spring-loaded against the covering member upon installation of the fitting on the flange.

In an advantageous embodiment, the fitting comprises a shut-off valve. This may especially be advantageous if no shielding and covering members are provided in the fitting, or if both high and low pressures may occur in the vessel or pipe of the processing installation. In the latter case the shut-off valve ensures that the shielding member is not lifted from the covering member as a result of a pressure difference between the internal of the processing system and the exterior surroundings.

In a further embodiment, the sampling device comprises a nozzle adapted to be connected to the fitting and having an internal projection adapted to keep the shielding member displaced against the spring-load in the connected state of the nozzle to the fitting, and the nozzle has a tube connection for supply or discharge of cleaning or washing fluid. Thereby the interior of the fitting may be cleaned or washed after the taking of a sample.

The present invention also relates to a sampling device comprising a sampling container for reception of a sample volume and a connecting piece adapted to be connected to a fitting mounted on a vessel or pipe of a processing installation or the like, the connecting piece having a sample passage which is provided with a stationary valve part and a corresponding valve member which is displaceable between a closed position, in which it abuts the stationary valve part and closes the sample passage, and an open position, in which the sample passage is open, wherein the sampling container comprises an outer container and an inner container, the inner container being arranged displaceably in a longitudinal direction of the outer container, the outer container at a first end is formed integrally with the connecting piece and at a second end is provided with a bottom, the inner container at a first end is formed integrally with an annular sealing surface, thereby forming the displaceable valve member, and at a second end has a bottom in which a spindle passage is provided, a spindle has a first end which is provided with the stationary valve part and a second end which is fixed to the bottom of the outer container, and the spindle passage is arranged tightly around and displaceably along the spindle.

In another embodiment, the sampling device comprises a fitting mating the connecting piece and having an installation end adapted to be installed onto the vessel or pipe of said processing installation or the like, the fitting has a tubular part provided with an inner shielding member adapted to shield the stationary valve part in the connected state of the connecting piece and the fitting, the tubular part of the fitting is provided with a covering member adapted to cover the displaceable valve member in the connected state of the connecting piece and the fitting, and the shielding member is adapted to seal against the covering member in the disconnected state of the connecting piece and the fitting.

The present invention also relates to a sampling method for taking a sample of a product from a processing installation or the like, comprising the steps of connecting a connecting piece of a sampling device to a fitting mounted on a vessel or pipe of the processing installation or the like, displacing a valve member in a sample passage of the connecting piece from a closed position, in which it closes the sample passage, to an open position, in which the sample passage is open, allowing product to pass from the processing installation or the like, through the sample passage, and into a sampling container of the sampling device, displacing the valve member from its open position to its closed position, and disconnecting the connecting piece from the fitting.

The sampling method is characterized by that the valve member is displaced in the sampling container from its closed position to its open position against a spring-load, and by that the valve member is automatically displaced to its open position upon connection of the connecting piece with the fitting. Thereby the above-mentioned advantages are obtained.

In a further embodiment of the sampling method, the valve member is displaced to its open position by means of a covering member fixedly mounted in the fitting and abutting the valve member during at least part of the operation of connecting the connecting piece to the fitting, whereby a circumferential contour of the covering member fits a circumferential contour of the valve member, by that a shielding member mounted displaceably in the fitting abuts the stationary valve part, whereby a circumferential contour of the shielding member fits a circumferential contour of the stationary valve part, and whereby the shielding member is displaced against a spring-load during at least part of the operation of connecting the connecting piece to the fitting, and by that, after disconnecting the connecting piece from the fitting, the circumferential contour of the shielding member fits the circumferential contour of the covering member, and the circumferential contour of the stationary valve part fits the circumferential contour of the displaceable valve member. Thereby a sample may be taken out in a fully contained way as explained above.

In a further embodiment of the sampling method, a shut-off valve of the fitting is opened and subsequently closed in the fully connected state of the connecting piece and the fitting in order to allow the product to pass through the fitting. Thereby the above-mentioned advantages are obtained.

In a further embodiment of the sampling method, in the disconnected state of the connecting piece and the fitting, a nozzle is connected to the fitting, whereby an internal projection in the nozzle keeps the shielding member displaced against the spring-load in the connected state of the nozzle to the fitting, and a cleaning or washing fluid is supplied to or discharged from the fitting through the nozzle. Thereby the above-mentioned advantages are obtained.

BRIEF DESCRIPTION OF THE SEVERAL VIEWS OF THE DRAWING

The invention will be described in more detail below by means of examples of embodiments with reference to the schematic drawing, in which.

DETAILED DESCRIPTION OF THE INVENTION

Figure 1:
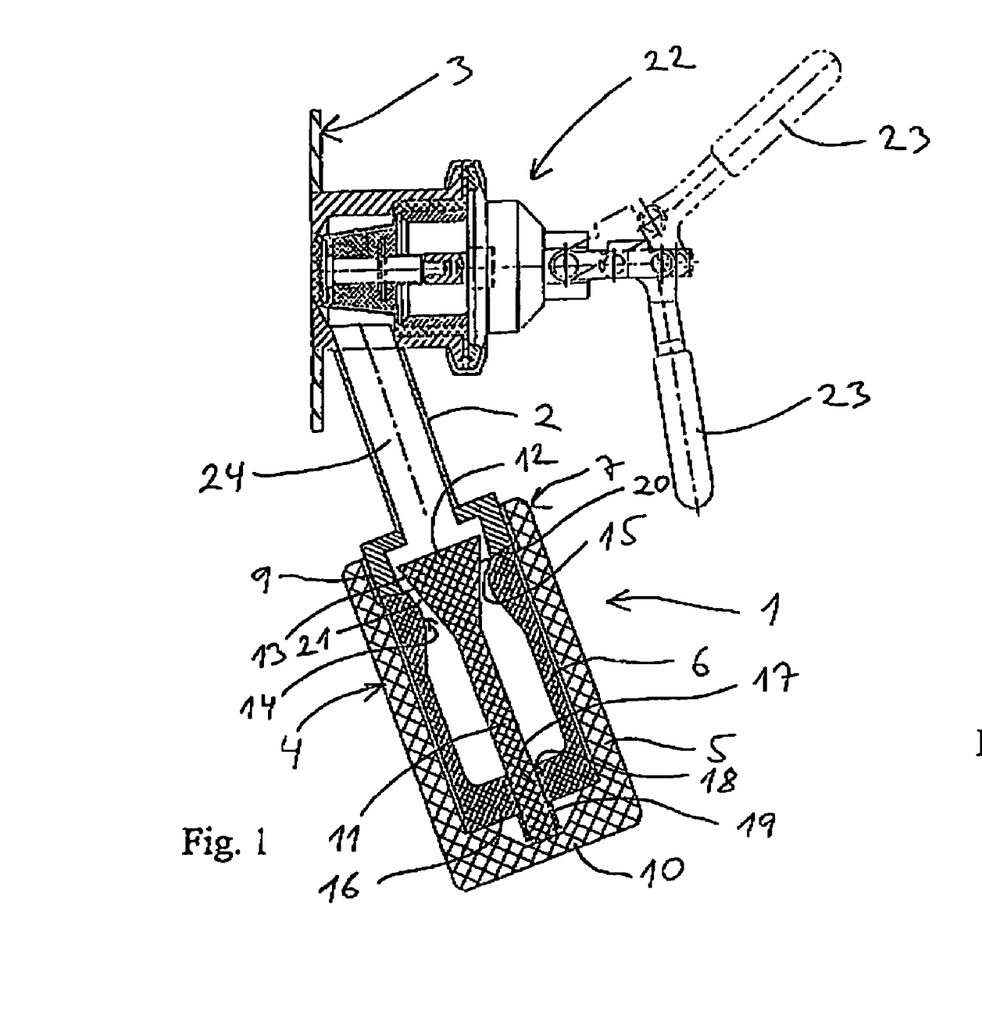
FIG. 1 is a partially sectional view of a sampling device according to the invention, connected to a fitting.

FIG. 1 shows a sampling device 1 according to the invention, connected to a fitting 2 mounted on a vessel 3 of a processing installation of which is shown only part of a wall. The sampling device 1 has a sampling container 4 comprising an outer cylindrical container 5 and an inner cylindrical container 6 arranged concentric inside the outer container 5 so that it is displaceable in the axial direction of the latter.

The sampling device 1 and the method of sampling according to the invention may be used in all industries, e.g. such as pharmaceutical, biotechnological and chemical, for all kinds of processing equipment or storage containers as well as pipe systems, and for all kinds of products, e.g. such as powders, granules, liquid products and gaseous products, as well as any possible combination of products. For powders and granules, the processing installation to take samples from may e.g. be fluid bed equipment, granulation equipment, agglomeration equipment, coating equipment, layering equipment, extrusion equipment, spray drying equipment, packaging equipment etc. Furthermore, heavy, sticky or viscous products or products having limited flow capabilities may be sampled by means of the device and the sampling method according to the invention.

At a first end, the outer container 5 is formed integrally with a connecting piece 7 in the form of an internal thread 8 which in FIG. 1 has been screwed onto an outer thread 9 of the fitting 2. At a second end, the outer container 5 has a bottom 10, to which a spindle 11 is fixed rigidly and from which the spindle 11 extends coaxially in the outer container 5 to the area of the first end of the outer container, where a stationary valve part 12 in the form of a truncated cone is formed integrally with the spindle 11 and concentric with this. The stationary valve part 12 has a conical sealing surface 13 facing the interior of the sampling container 4.

At a first end, the inner container 6 is formed integrally with a displaceable valve member 14 in the form of a conical sealing surface 15 facing away from the interior of the sampling container 4 and corresponding to the conical sealing surface 13 of the stationary valve part 12. At a second end, the inner container 6 has a bottom 16 in which is formed a concentric spindle passage 17 sealed displaceably against the spindle 11 by means of an O-ring 18.

Figure 2:
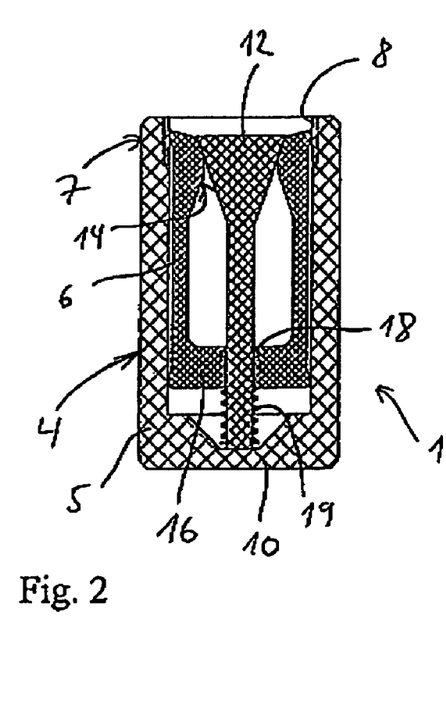
FIG. 2 is a sectional view of the sampling device in FIG. 1, after disconnection from the fitting.

Between the bottom 16 of the inner container 6 and the bottom 10 of the outer container 5 is arranged a compression spring 19 around the spindle 11, thereby spring-loading the inner container 6 with its integral valve member 14 towards a closed position of the displaceable valve member 14, in which position the conical sealing surface 15 of the valve member 14 abuts the conical sealing surface 13 of the stationary valve part 12, as shown in FIG. 2 where the sampling container 4 has been disconnected from the fitting 2.

In the connected state of the connecting piece 7 to the fitting 2, as shown in FIG. 1, the valve member 14 formed on the internal container 6 abuts an edge 20 of the fitting 2, whereby the valve member 14 is maintained in its open position displaced against the load of the compression spring 19 so that a passage 21 is open between the displaceable valve member 14 and the stationary valve part 12.

In order to take a sample from the vessel 3, the closed sampling container 4 shown in FIG. 2 is screwed onto the fitting 2 whereby the displaceable valve member 14 is displaced to its open position shown in FIG. 1. Subsequently, a shut-off valve 22 comprised by the fitting 2 is operated manually by means of a handle 23 so that product may pass from the interior of the vessel 3 to an internal tubular part 24 of the fitting 2 and into the open sampling container 4. The open position of the handle 23 is indicated by means of dash-dot lines. The outer and inner containers 5, 6 may advantageously be formed from Plexiglass®, glass, tempered glass or the like, whereby the amount of product entering the sampling container 4 may be observed visually. After having taken an appropriate sample, the shut-off valve 22 is closed and the sampling container 4 is screwed off the fitting 2 whereby the valve member 14 is displaced to its closed position as shown in FIG. 2. Subsequently, the sampling container 4 may be handled without risk of product leakage and possibly transported before the sample is poured out of the container 4. In order to pour out the product contained in the sampling container 4, the container may be screwed on a suitable laboratory equipment having a part fitting the connecting piece 7 similar to the fitting 2, i.e. having an outer thread similar to the thread 9 and an edge similar to the edge 20 adapted to abut the displaceable valve member 14 and thereby maintain this in its open position.

Figure 3:
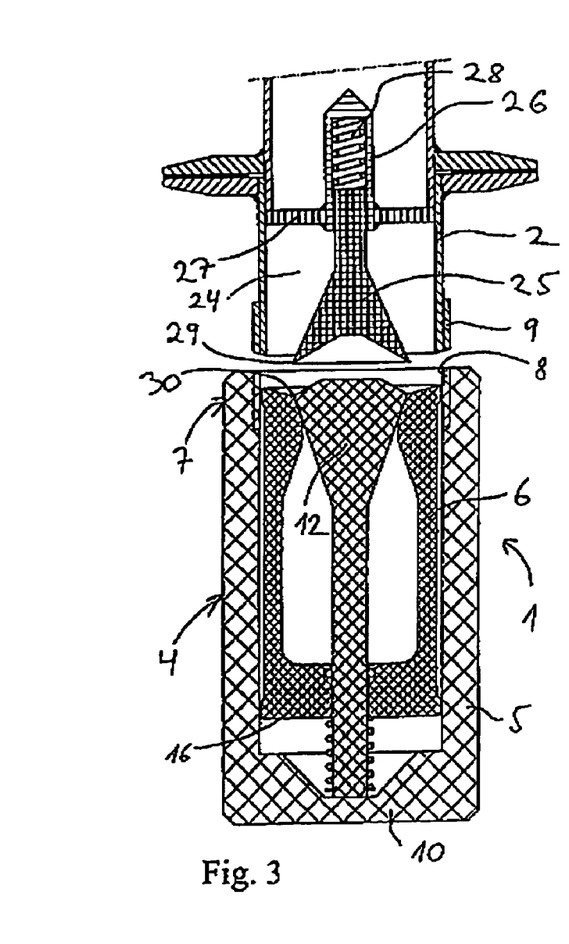
FIGS. 3 and 4 are sectional views of other embodiments of the sampling device.

FIG. 3 shows another embodiment of the sampling device according to the invention. The embodiment differs from the one shown in FIG. 1 in that the fitting 2 is provided with an internal shielding member 25 which is guided in a tube element 26 fixed in a plate 27 which is guided and axially displaceable in the tubular part 24 of the fitting 2. By means of a compression spring 28 located in the tube element 26, the shielding member 25 is spring-loaded to abut the stationary valve part 12 upon connection of the connecting piece 7 to the fitting 2. The shielding member 25 has a circumferential contour 29 fitting a circumferential contour 30 of the stationary valve part 12.

Figure 6:
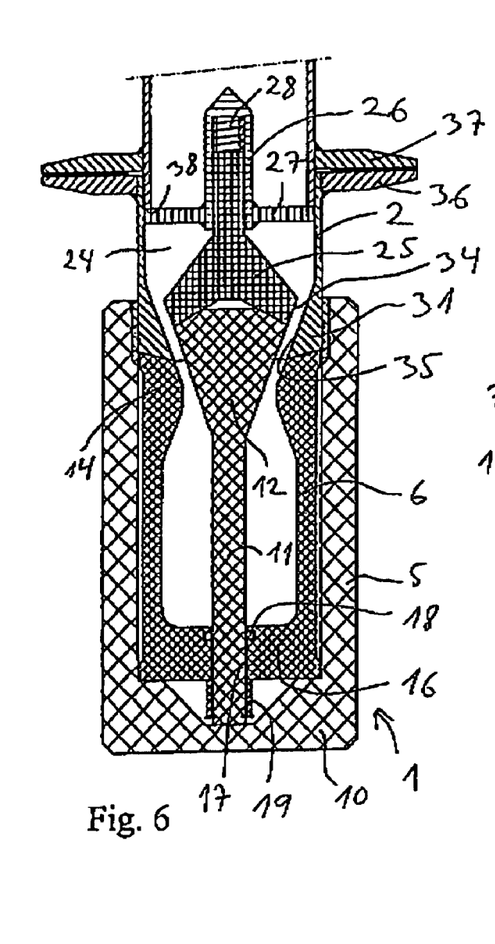
FIGS. 6 to 8 are sectional views of a further embodiment of the sampling device, in the connected state of the connecting piece on the fitting, in the partially disconnected state, and in the fully disconnected state, respectively.
Figure 7:
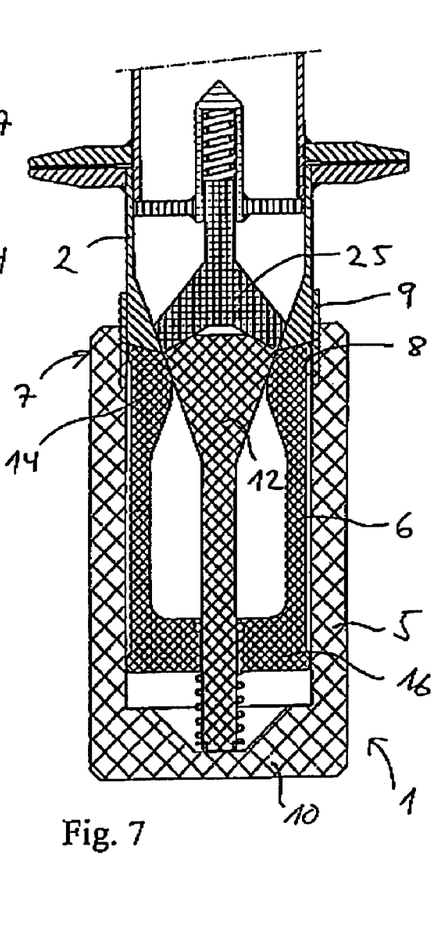
Figure 8:
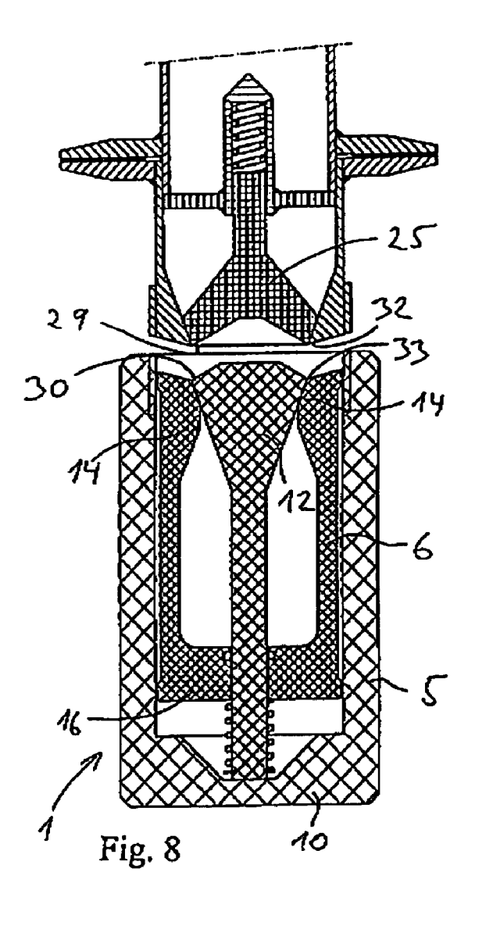

FIGS. 6 to 8 show another embodiment of the sampling device 1. The embodiment differs from the one shown in FIG. 1 in that the fitting 2 furthermore is provided with both a shielding member 25 and a covering member 31 formed integrally with the tubular part 24 of the fitting 2. The covering member 31 has a circumferential contour 32 fitting both a circumferential contour 33 of the displaceable valve member 14 and a circumferential contour 29 of the shielding member 25. The stationary valve part 12 has a circumferential contour 30 fitting both the circumferential contour 33 of the displaceable valve member 14 and the circumferential contour 29 of the shielding member 25. Furthermore, the shielding member 25 has a conical sealing surface 34 corresponding to a conical sealing surface 35 of the covering member 31. FIG. 6 shows the connected state of the connecting piece 7 of the sampling container 4 on the fitting 2, in which state the displaceable valve member 14 and the shielding member 25 are in their open positions. FIG. 7 shows a partly disconnected state of the connecting piece 7 and the fitting 2, in which state both the displaceable valve member 14 and the shielding member 25 are in their closed positions and the thread 8 of the connecting piece 7 is engaging the thread 9 of the fitting 2 in order to secure tight connection between the sampling container 4 and the fitting 2. FIG. 8 shows the disconnected state of the connecting piece 7 and the fitting 2, in which state the displaceable valve member 14 and the shielding member 25 are in their closed positions. With this embodiment it is possible to take a sample in a fully contained way so that the surroundings and the operator are practically not exposed to the product sampled. After having taken the sample, the sampling container 4 may, as explained above, be transported to and screwed on a suitable laboratory equipment whereby the product sampled may be transferred to said equipment, also in a fully contained way.

In a typical execution, the outer container 5 has an outer length of approximately 130 mm, an outer diameter of approximately 75 mm and a wall thickness of approximately 10 mm and the inner container 6 has an inner diameter of approximately 40 mm and an inner length between its bottom 16 and its annular sealing surface 15 of approximately 65 mm. In this execution, the length of the internal thread 8 of the outer container 5 is approximately 18 mm and the outer length of the fitting 2 is approximately 53 mm. The diameter of the circumferential contour 32 of the covering member 31 fitting the circumferential contour 29 of the shielding member 25 is approximately 34 mm. In another typical execution, said dimensions have been multiplied by two. The dimensions and the materials may also typically be chosen so as to ensure that the device is explosion proof for a required pressure.

The embodiments of the sampling device 1 shown in FIGS. 1 to 3 and 6 to 8 are especially suitable if the pressure in the vessel or pipe of the processing installation to be sampled from is below atmospheric, as substantially the same pressure will be present in the sampling container 4 after having taken the sample. Consequently, the pressure difference between the surroundings and the internal of the sampling container 4 will assist the spring 19 in keeping the valve member 14 in its closed position after taking the sample and disconnecting the container 4 from the fitting 2.

Figure 5:
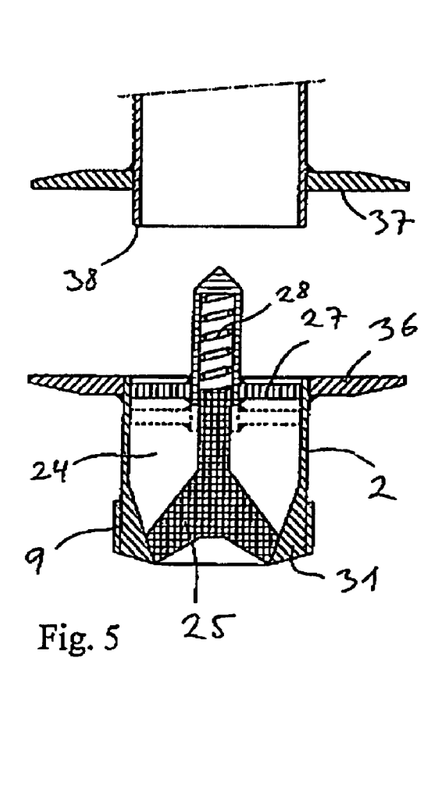
FIG. 5 is a sectional view of a flange and a fitting for connection to the sampling device, before mounting the fitting on the flange.

FIG. 5 shows the fitting 2 of the sampling device 1 in FIGS. 6 to 8, before mounting a flange 36 of the fitting 2 on a flange 37 of the processing installation. As indicated by means of dash-dot lines, the plate 27 is displaceable axially in the tubular part 24 of the fitting 2 and upon connection of the flange parts 36, 37, an edge 38 of the vessel of the processing installation will abut the plate 27, thereby displacing the plate to the position indicated by means of the dash-dot lines, whereby the compression spring 28 will be compressed and thereby preload the shielding member 25 against the covering member 31.

Figure 4:
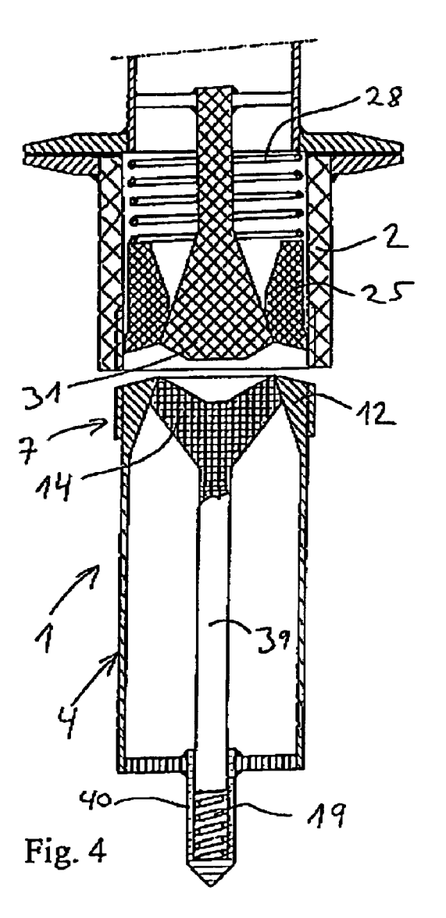

FIG. 4 shows still another embodiment of the sampling device 1 according to the invention. In this embodiment parts similar to parts in the embodiment in FIGS. 6 to 8 are indicated with similar reference numbers. The sampling container 4 has an annular stationary valve part 12 formed integrally around its inlet opening. The displaceable valve member 14 is by means of a spindle 39 guided in a tube element 40 at the bottom of the sampling container 4. The fitting 2 is provided with a spring-loaded annular displaceable shielding member 25 and a conical fixed covering member 31. This embodiment also permits the taking of samples in a fully contained way and is especially suitable if the pressure in the vessel or pipe of the processing installation to be sampled from is above atmospheric, as substantially the same pressure will be present in the sampling container 4 after having taken the sample. Consequently, the pressure difference between the surroundings and the internal of the sampling container 4 will assist the spring 19 in keeping the valve member 14 in its closed position after taking the sample and disconnecting the container 4 from the fitting 2. This will prevent even a small amount of product in leaking upon disconnection of the sampling container 4 from the fitting 2.

The embodiments shown in FIGS. 4 and 6 to 8 may be used with or without the shut-off valve 22 shown in FIG. 1, depending on the situation, for instance whether the pressure in the installation to be sampled from is constantly above or below atmospheric or may change.

Figure 9:
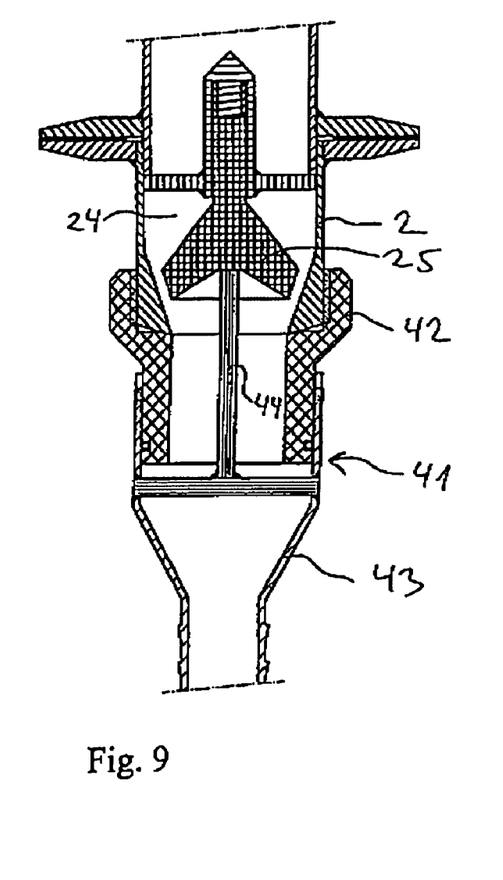
FIGS. 9 to 11 are sectional views of a nozzle of the sampling device, in the connected state of the nozzle on the fitting, in the partially disconnected state, and in the fully disconnected state, respectively.
Figure 10:
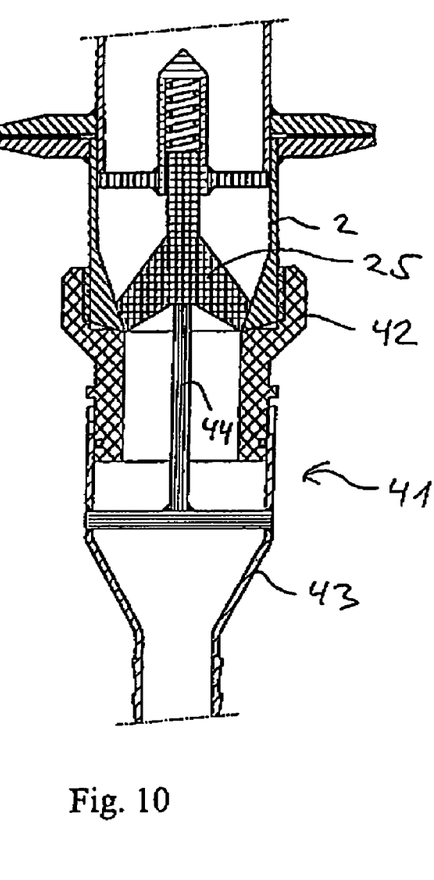
Figure 11:
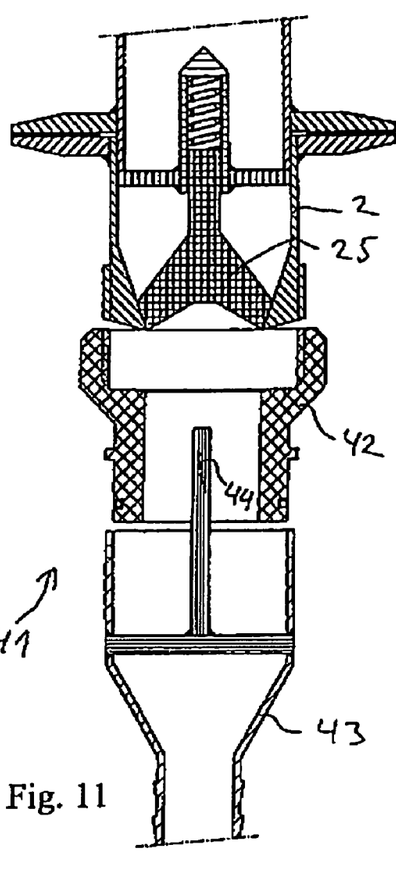

FIGS. 9 to 11 show an embodiment of the sampling device 1 comprising a nozzle 41 comprising a connecting piece 42 which may be connected with the fitting 2 and which has a tube connection 43 for the supply of or discharge of cleaning or washing fluid to or from the fitting 2. The tube connection 43 comprises an internal projection 44 which in the connected state of the nozzle 41 on the fitting 2 maintains the shielding member 25 in its open position, thereby allowing cleaning or washing fluid to pass in or out through the fitting 2. FIG. 9 shows the connected state, FIG. 10 shows a partly connected state, in which the connecting piece 42 is mounted on the fitting 2, but in which the tube connection 43 is not fully connected to the connecting piece 42 so that the shielding member 25 is still in its closed position, and FIG. 11 shows the fully disconnected state.

The invention claimed is:

1. A sampling device comprising a sampling container for reception of a sample volume and a connecting piece adapted to be connected to a fitting mounted on a vessel or pipe of a processing installation, the connecting piece having a sample passage which is provided with a stationary valve part and a corresponding valve member which is displaceable between a closed position, in which it abuts the stationary valve part and closes the sample passage, and an open position, in which the sample passage is open, the stationary valve part and the valve member being integrated in the sampling container, and the valve member being spring-loaded towards its closed position and adapted to be automatically displaced to its open position upon connection of the connecting piece with the fittings, wherein the connecting piece is adapted to be screwed onto the fitting.

2. A sampling device according to claim 1, wherein the displaceable valve member has a conical sealing surface corresponding to a conical sealing surface on the stationary valve part.

3. A sampling device according to claim 1, wherein the connecting piece is adapted to be displaced in a longitudinal direction of the container during at least part of the operation of connecting it to the fitting, and the displaceable valve member is adapted to abut an edge of the fitting during at least part of said displacement.

4. A sampling device according to claim 1, wherein the sampling container comprises an outer container and an inner container, the inner container being arranged displaceably in a longitudinal direction of the outer container, the outer container at a first end is formed integrally with the connecting piece and at a second end is provided with a bottom, the inner container at a first end is formed integrally with an annular sealing surface, thereby forming the displaceable valve member, and at a second end has a bottom in which a spindle passage is provided, a spindle has a first end which is provided with the stationary valve part and a second end which is fixed to the bottom of the outer container, and the spindle passage is arranged tightly around and displaceably along the spindle.

5. A sampling device according to claim 4, wherein the outer length of the outer container is between 100 mm and 300 mm, the outer diameter of the outer container is between ½ and ⅔ of the outer length of the outer container, and the smallest diameter of the annular sealing surface of the inner container is between ¼ and ⅔ of the outer diameter of the outer container.

6. A sampling device according to claim 4, wherein the outer container and the inner container are formed from Plexiglass, glass, tempered glass, and the stationary valve part is formed from polytetrafluoroethylene.

7. A sampling device according to claim 1, wherein the sampling device comprises a fitting mating the connecting piece and having an installation end adapted to be installed onto the vessel or pipe of said processing installation, and the fitting has a tubular part provided with an inner shielding member adapted to shield the stationary valve part in the connected state of the connecting piece and the fitting.

8. A sampling device according to claim 7, wherein the tubular part of the fitting is provided with a covering member adapted to cover the displaceable valve member in the connected state of the connecting piece and the fitting.

9. A sampling device according to claim 8, wherein the shielding member is adapted to seal against the covering member in the disconnected state of the connecting piece and the fitting.

10. A sampling device according to claim 8, wherein a circumferential contour of the shielding member fits a circumferential contour of the stationary valve part, the shielding member is adapted to be displaced with the stationary valve part against a spring-load during at least part of the operation of connecting the connecting piece to the fitting, a circumferential contour of the covering member fits a circumferential contour of the displaceable valve member, the covering member is fixedly mounted in the fitting, the circumferential contour of the shielding member fits the circumferential contour of the covering member, and the circumferential contour of the stationary valve part fits the circumferential contour of the displaceable valve member.

11. A sampling device according to claim 8, wherein the shielding member has a conical sealing surface corresponding to a conical sealing surface on the covering member.

12. A sampling device according to claim 8, wherein the shielding member is spring-loaded against the covering member by means of a spring located in a tube element in which a spindle of the shielding member is guided, the tube element is guided axially in the tubular part of the fitting, and the tube element is fixed in a plate adapted to abut an edge of a flange on the vessel or pipe of the processing installation, in the mounted state of the fitting on said flange.

13. A sampling device according to claim 7, wherein the fitting comprises a shut-off valve.

14. A sampling device according to claim 9, wherein the sampling device comprises a nozzle adapted to be connected to the fitting and having an internal projection adapted to keep the shielding member displaced against the spring-load in the connected state of the nozzle to the fitting, and the nozzle has a tube connection for supply or discharge of cleaning or washing fluid.

15. A sampling method for taking a sample of a product from a processing installation, comprising the steps of connecting a connecting piece of a sampling device to a fitting mounted on a vessel or pipe of the processing installation, displacing a valve member in a sample passage of the connecting piece from a closed position, in which it closes the sample passage, to an open position, in which the sample passage is open, allowing product to path from the processing installation, through the sample passage, and into a sampling container of the sampling device, displacing the valve member from its open position to its closed position, and disconnecting the connecting piece from the fitting, whereby the valve member is displaced in the sampling container from its closed position to its open position against a spring-load, and the valve member is automatically displaced to its open position upon connection of the connecting piece with the fitting, whereby the valve member is displaced to its open position by means of a covering member fixedly mounted in the fitting and abutting the valve member during at least part of the operation of connecting the connecting piece to the fitting, whereby a circumferential contour of the covering member fits a circumferential contour of the valve member, a shielding member mounted displaceably in the fitting abuts the stationary valve part, whereby a circumferential contour of the shielding member fits a circumferential contour of the stationary valve part, and whereby the shielding member is displaced against a spring-load during at least part of the operation of connecting the connecting piece to the fitting, and whereby, after disconnecting the connecting piece from the fitting, the circumferential contour of the shielding member fits the circumferential contour of the covering member, and the circumferential contour of the stationary valve part fits the circumferential contour of the displaceable valve member.

16. A sampling method according to claim 15, whereby a shut-off valve of the fitting is opened and subsequently closed in the fully connected state of the connecting piece and the fitting in order to allow the product to pass through the fitting.

17. A sampling method according to claim 15, whereby, in the disconnected state of the connecting piece and the fitting, a nozzle is connected to the fitting, whereby an internal projection in the nozzle keeps the shielding member displaced against the spring-load in the connected state of the nozzle to the fitting, and a cleaning or washing fluid is supplied to or discharged from the fitting through the nozzle.

18. A sampling device according to claim 2, wherein the sampling device comprises a fitting mating the connecting piece and having an installation end adapted to be installed onto the vessel or pipe of said processing installation, and the fitting has a tubular part provided with an inner shielding member adapted to shield the stationary valve part in the connected state of the connecting piece and the fitting.

19. A sampling device according to claim 3, wherein the sampling device comprises a fitting mating the connecting piece and having an installation end adapted to be installed onto the vessel or pipe of said processing installation, and the fitting has a tubular part provided with an inner shielding member adapted to shield the stationary valve part in the connected state of the connecting piece and the fitting.

20. A sampling device according to claim 4, wherein the sampling device comprises a fitting mating the connecting piece and having an installation end adapted to be installed onto the vessel or pipe of said processing installation, and the fitting has a tubular part provided with an inner shielding member adapted to shield the stationary valve part in the connected state of the connecting piece and the fitting.

21. A sampling device according to claim 5, wherein the sampling device comprises a fitting mating the connecting piece and having an installation end adapted to be installed onto the vessel or pipe of said processing installation, and the fitting has a tubular part provided with an inner shielding member adapted to shield the stationary valve part in the connected state of the connecting piece and the fitting.

22. A sampling device according to claim 6, wherein the sampling device comprises a fitting mating the connecting piece and having an installation end adapted to be installed onto the vessel or pipe of said processing installation, and the fitting has a tubular part provided with an inner shielding member adapted to shield the stationary valve part in the connected state of the connecting piece and the fitting.

23. A sampling device comprising a sampling container for reception of a sample volume and a connecting piece adapted to be connected to a fitting mounted on a vessel or pipe of a processing installation, the connecting piece having a sample passage which is provided with a stationary valve part and a corresponding valve member which is displaceable between a closed position, in which it abuts the stationary valve part and closes the sample passage, and an open position, in which the sample passage is open, the stationary valve part and the valve member being integrated in the sampling container, and the valve member being spring-loaded towards its closed position and adapted to be automatically displaced to its open position upon connection of the connecting piece with the fitting, wherein the sampling container comprises an outer container and an inner container, the inner container being arranged displaceably in a longitudinal direction of the outer container, the outer container at a first end is formed integrally with the connecting piece and at a second end is provided with a bottom, the inner container at a first end is formed integrally with an annular sealing surface, thereby forming the displaceable valve member, and at a second end has a bottom in which a spindle passage is provided, a spindle has a first end which is provided with the stationary valve part and a second end which is fixed to the bottom of the outer container, and the spindle passage is arranged tightly around and displaceably along the spindle, and wherein the outer length of the outer container is between 100 mm and 300 mm, the outer diameter of the outer container is between ½ and ⅔ of the outer length of the outer container, and the smallest diameter of the annular sealing surface of the inner container is between ¼ and ⅔ of the outer diameter of the outer container.

24. A sampling device comprising a sampling container for reception of a sample volume and a connecting piece adapted to be connected to a fitting mounted on a vessel or pipe of a processing installation, the connecting piece having a sample passage which is provided with a stationary valve part and a corresponding valve member which is displaceable between a closed position, in which it abuts the stationary valve part and closes the sample passage, and an open position, in which the sample passage is open, the stationary valve part and the valve member being integrated in the sampling container, and the valve member being spring-loaded towards its closed position and adapted to be automatically displaced to its open position upon connection of the connecting piece with the fitting, wherein the sampling device comprises a fitting mating the connecting piece and having an installation end adapted to be installed onto the vessel or pipe of said processing installation and the fitting has a tubular part provided with an inner shielding member adapted to shield the stationary valve part in the connected state of the connecting piece and the fitting, wherein the tubular part of the fitting is provided with a covering member adapted to cover the displaceable valve member in the connected state of the connecting piece and the fitting, and wherein a circumferential contour of the shielding member fits a circumferential contour of the stationary valve part, the shielding member is adapted to be displaced with the stationary valve part against a spring-load during at least part of the operation of connecting the connecting piece to the fitting, a circumferential contour of the covering member fits a circumferential contour of the displaceable valve member, the covering member is fixedly mounted in the fitting, the circumferential contour of the shielding member fits the circumferential contour of the covering member, and the circumferential contour of the stationary valve part fits the circumferential contour of the displaceable valve member.

25. A sampling device comprising a sampling container for reception of a sample volume and a connecting piece adapted to be connected to a fitting mounted on a vessel or pipe of a processing installation, storage container or pipe system, the connecting piece having a sample passage which is provided with a stationary valve part and a corresponding valve member which is displaceable between a closed position in which it abuts the stationary valve part and closes the sample passage, and an open position, in which the sample passage is open, the stationary valve part and the valve member being integrated in the sampling container, the valve member being spring-loaded towards its closed position and adapted to be automatically displaced to its open position upon connection of the connecting piece with the fitting, the stationary valve part or the valve member being formed as a conical face forming part of a wall surrounding the inside volume of the sampling container, and the other one of said stationary valve part and said valve member having the form of a truncated cone carried by a spindle extending coaxially through the inside volume of the sampling container.

26. A sampling method for taking a sample of a product from a processing installation, storage container or pipe system, comprising the steps of:
  connecting a connecting piece of a sampling device to a fitting mounted on a vessel or pipe of the processing installation, storage container or pipe system;
  displacing a valve member in a sample passage of the connecting piece from a closed position, in which it abuts a stationary valve part and thereby closes the sample passage, to an open position, in which the sample passage is open, allowing the product to pass from the processing installation, storage container or pipe system, through the sample passage, and into a sampling container of the sampling device;
  displacing the valve member from its open position to its closed position; and
  disconnecting the connecting piece from the fitting, whereby the valve member is displaced from its closed position to its open position against a spring-load, and whereby the valve member is automatically displaced to its open position upon connection of the connecting piece with the fitting, whereby, in the open position of the valve member, the product passes through a conical annular passage formed between a conical face forming part of a wall surrounding the inside volume of the sampling container and a truncated cone carried by a spindle extending coaxially through the inside volume of the sampling container.

* * * * *